US010357382B2

(12) United States Patent
Ballas et al.

(10) Patent No.: US 10,357,382 B2
(45) Date of Patent: Jul. 23, 2019

(54) ADAPTIVE COMPRESSION PROSTHETIC SOCKET SYSTEM AND METHOD

(71) Applicant: EPOCH MEDICAL INNOVATIONS, INC., Seattle, WA (US)

(72) Inventors: Michael Thomas Ballas, Seattle, WA (US); Gary Joseph Ballas, Seattle, WA (US)

(73) Assignee: Epoch Medical Innovations, Inc., Seattle, WA (US)

(*) Notice: Subject to any disclaimer, the term of this patent is extended or adjusted under 35 U.S.C. 154(b) by 0 days.

(21) Appl. No.: 14/855,248

(22) Filed: Sep. 15, 2015

(65) Prior Publication Data

US 2016/0000583 A1    Jan. 7, 2016

Related U.S. Application Data

(63) Continuation of application No. PCT/US2014/029619, filed on Mar. 14, 2014.

(60) Provisional application No. 61/793,381, filed on Mar. 15, 2013.

(51) Int. Cl.
*A61F 2/80* (2006.01)
*A61F 2/74* (2006.01)
(Continued)

(52) U.S. Cl.
CPC .................. *A61F 2/68* (2013.01); *A61F 2/76* (2013.01); *A61F 2/7812* (2013.01);
(Continued)

(58) Field of Classification Search
CPC ............ A61F 2/7843; A61F 2002/5032; A61F 2002/785
(Continued)

(56) References Cited

U.S. PATENT DOCUMENTS 6,585,774 B2    7/2003  Dean, Jr. et al.
2002/0099450 A1*  7/2002  Dean, Jr. .................. A61F 2/76
                                                                     623/26
(Continued)

FOREIGN PATENT DOCUMENTS

SU            425629 A  *  2/1975  ............... A61F 2/80

OTHER PUBLICATIONS

International Search Report, dated Aug. 15, 2014, for International Application No. PCT/US2014/029619, 2 pages.
(Continued)

*Primary Examiner* — David H Willse
(74) *Attorney, Agent, or Firm* — Seed IP Law Group LLP

(57) ABSTRACT

An incompressible fluid is used to adjust fit for a prosthetic device, the use of a closed loop control system and force, motion, and position measurement to aid with algorithms controlling the fit of the prosthetic device to a residual limb. Embodiments include automatic actuation, based on triggering of threshold values from sensors, a powered full release feature, use of hydraulic transducers to transfer fluid pressure to force on a limb, and customizable pressure distribution pads and embedded valves in transducers to prevent backflow and allow stabilization of the residual limb. A retrofit system may be used for existing prosthetic sockets. A triggering algorithm utilizes measured force exceeding a threshold or thresholds with a characteristic pulse signature and a triggering of release based on a combination of total motion and measured force below a threshold or thresholds.

8 Claims, 15 Drawing Sheets

(51) Int. Cl.
*A61F 2/70* (2006.01)
*A61F 2/68* (2006.01)
*A61F 2/78* (2006.01)
*A61F 2/76* (2006.01)
*A61F 2/50* (2006.01)

(52) U.S. Cl.
CPC .............. *A61F 2/7843* (2013.01); *A61F 2/80* (2013.01); *A61F 2002/5012* (2013.01); *A61F 2002/5032* (2013.01); *A61F 2002/745* (2013.01); *A61F 2002/747* (2013.01); *A61F 2002/802* (2013.01)

(58) Field of Classification Search
USPC .......................................................... 623/37
See application file for complete search history.

(56) References Cited

U.S. PATENT DOCUMENTS

| | | |
|---|---|---|
| 2003/0181990 A1* | 9/2003 | Phillips ................. A61F 2/7843 623/37 |
| 2010/0312360 A1 | 12/2010 | Caspers |
| 2011/0247321 A1 | 10/2011 | Streeter et al. |
| 2012/0065561 A1 | 3/2012 | Ballas et al. |
| 2012/0143351 A1 | 6/2012 | Tompkins |
| 2012/0271433 A1* | 10/2012 | Galea ................... A61F 2/7812 623/37 |

OTHER PUBLICATIONS

Written Opinion, dated Aug. 15, 2014, for International Application No. PCT/US2014/029619, 3 pages.

* cited by examiner

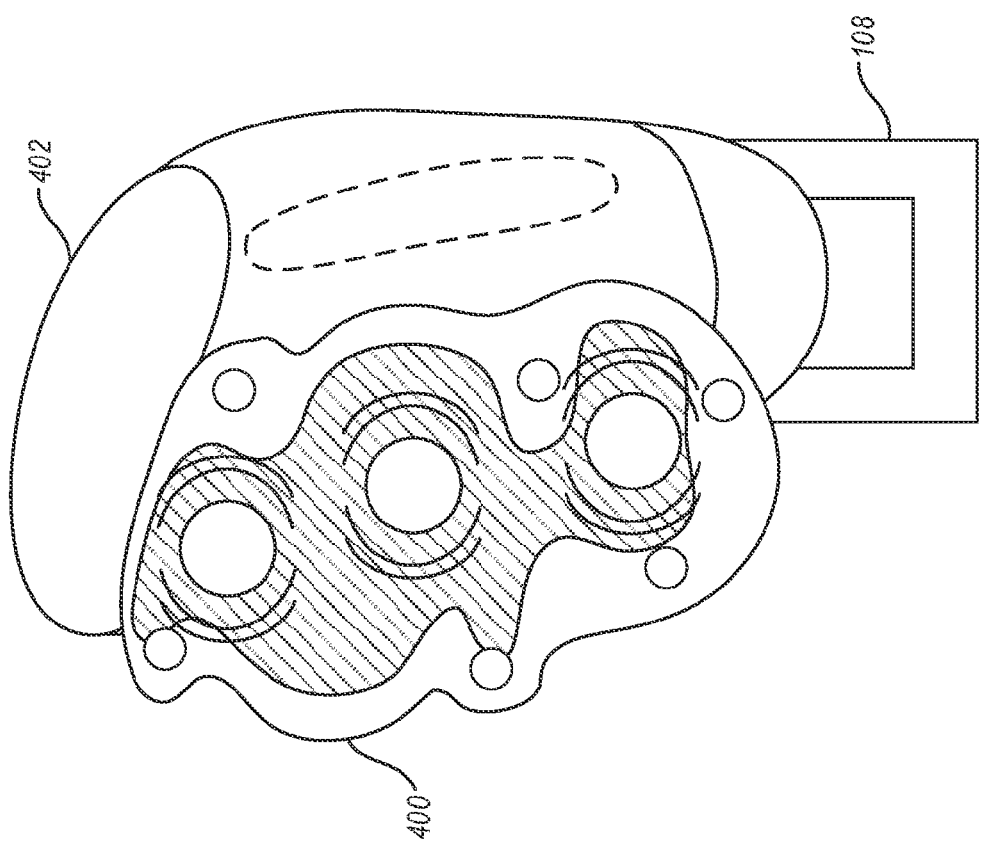

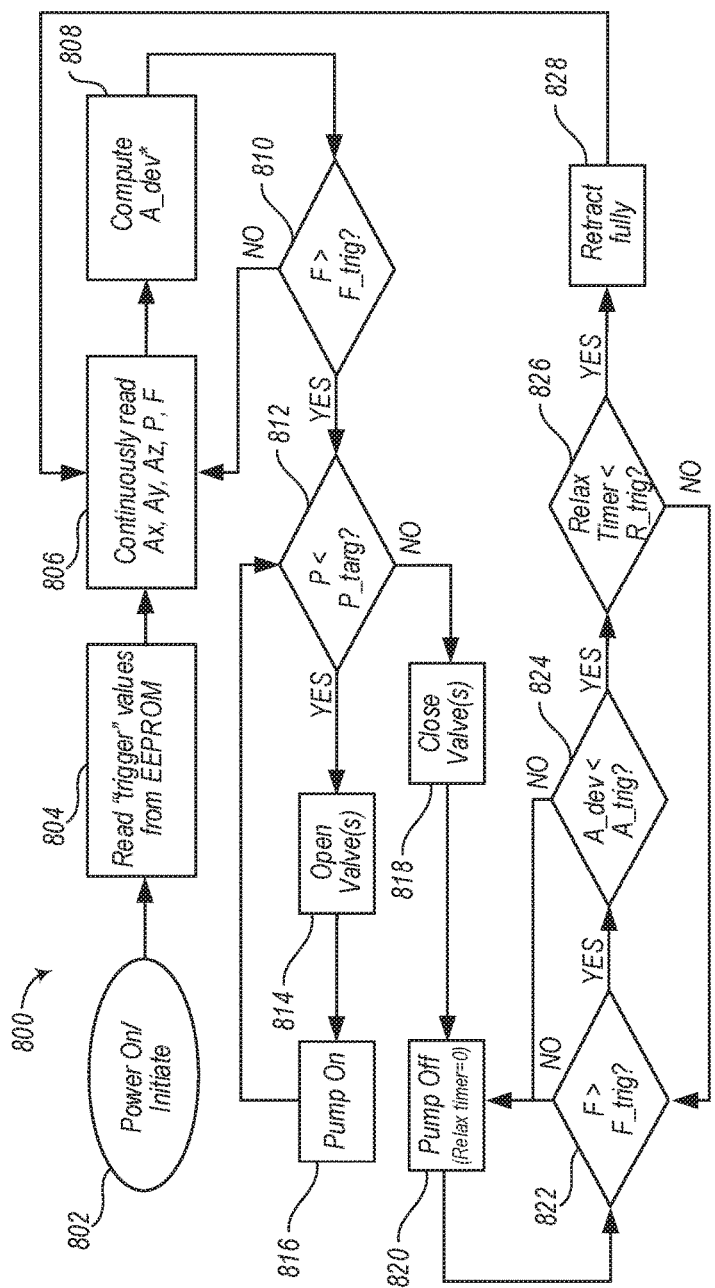

Ax, Ay, Az = Acceleration by x, y, z axes
P = Pressure in actuators
F = Force applied to socket from user $F\_trig$ = force threshold to signal loaded system
$P\_targ$ = target actuation pressure
$A\_trig$ = $A\_dev$ threshold to indicate active motive
$R\_trig$ = Relax timer threshold time to trigger release

*$A\_dev$ is the standard deviation of the total acceleration vector $(Ax^2 + Ay^2 + Az^2)^{1/2}$, computed over a moving window. It provides a measure of total motion and can be tuned for responsiveness by adjusting the moving window range.

ADAPTIVE COMPRESSION PROSTHETIC SOCKET SYSTEM AND METHOD

PRIORITY DATA

The present application claims the benefit of U.S. Provisional Patent Application No. 61/793,381, filed Mar. 15, 2013, which application is incorporated by reference herein in its entirety.

RELATED APPLICATION DATA

The present application is related to U.S. patent application Ser. No. 13/226,386, filed Sep. 6, 2011, which application is incorporated by reference herein in its entirety.

TECHNICAL FIELD

The present invention relates generally to prosthetics and more specifically to an adaptive control system for controlling the fit of a prosthetic device to a residual limb.

BACKGROUND

Many amputees are dissatisfied with the comfort and fit of their prosthetic device. Amputees typically have daily fluctuations in limb volume that result in improper fit of the sockets of their prosthetic devices, causing discomfort, skin breakdown, and instability during ambulation. The fit of the socket portion, which is the portion of the prosthetic device that fits around the amputated or "residual" limb, is very sensitive to changes in volume of the residual limb. When limb volume reduces, as commonly occurs throughout the day, the residual limb moves or "pistons" up and down in the socket, altering the fit of the socket and potentially inducing sores on the skin of the residual limb. Skin and underlying soft tissue injury is debilitating for the amputee, and can lead to secondary disability and a worsened quality of life.

In an attempt to try and accommodate for fluid volume loss of the residual limb, amputees may add socks, enlarge air-filled or liquid-filled bladders placed between the limb and socket, or use a vacuum pump to apply negative pressure to the residual limb and thus pull soft tissue outward towards the inner wall of the socket. Practically, however, most amputees do none of these things. This is true because the prosthesis must be removed to do so, which requires outer clothing also be removed. This is often socially unacceptable, disruptive, and time-consuming. Furthermore, technology may be viewed as "finicky" and unusable by non-technically-minded amputees. There is a need for improving the fit of a prosthetic device to a residual limb to thereby improve the comfort and quality of life of an amputee wearing the prosthetic device.

SUMMARY

In one embodiment of the present invention, a prosthetic device is operable to sense parameters including ambulatory state of a user along with force or pressure applied by the prosthetic device to a residual limb of the user, and to control hydraulic actuators responsive to the sensed parameters to control the fit of the prosthetic device on the residual limb. Each of the hydraulic actuators includes a plenum and a plurality of bellows actuator portions in one embodiment.

BRIEF DESCRIPTION OF THE FIGURES

FIG. 6E illustrates another view of the constricting actuator attached to the flexible socket of FIG. 4.

FIG. 8 is a flowchart illustrating a process executed by the controller of FIG. 1A according to one embodiment of the present invention.

DETAILED DESCRIPTION

Figure 1A:
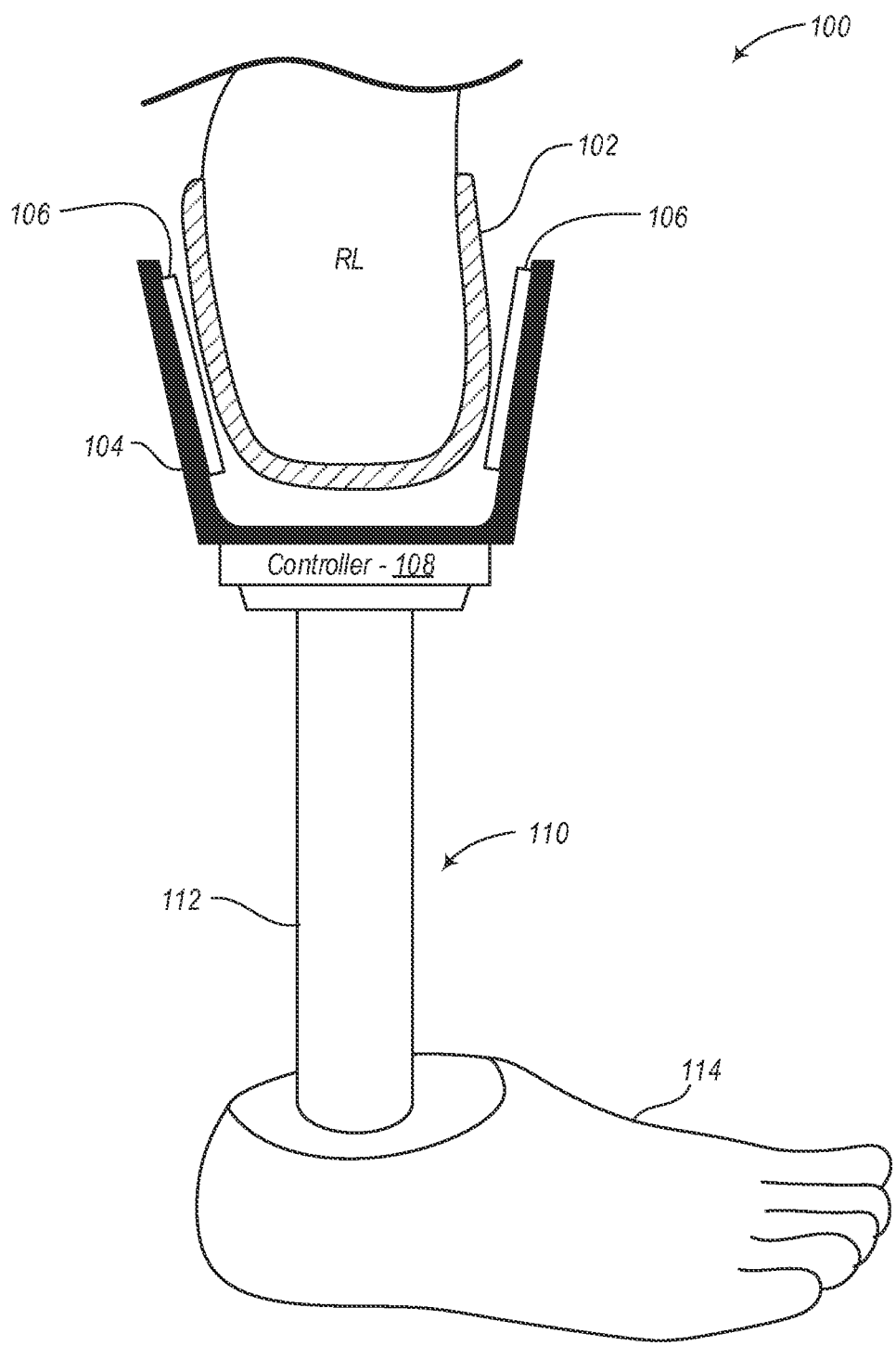
FIG. 1A is a cross-sectional view of a prosthetic device according to one embodiment of the present invention.

In the following description, certain details are set forth in conjunction with the described embodiments of the present invention to provide a sufficient understanding of the invention. One skilled in the art will appreciate, however, that the invention may be practiced without these particular details. Furthermore, one skilled in the art will appreciate that the example embodiments described below do not limit the scope of the present invention, and will also understand that various modifications, equivalents, and combinations of the disclosed embodiments and components of such embodiments are within the scope of the present invention. Embodiments including fewer than all the components of any of the respective described embodiments may also be within the scope of the present invention although not expressly described in detail below. Finally, the operation of well-known components and/or processes has not been shown or described in detail below so as to avoid unnecessarily obscuring the present invention.

Embodiments of the present invention are directed to the use of an incompressible fluid to adjust fit for a prosthetic device, the use of a closed loop control system, and force, motion, and position measurement to aid with algorithms controlling the fit of the prosthetic device to a residual limb. Embodiments also include automatic actuation, based on triggering of threshold values from sensors, a powered full release feature, use of hydraulic transducers to transfer fluid pressure to force on a limb, and customizable pressure distribution pads and embedded valves in transducers to prevent backflow and allow stabilization of the residual limb. Embodiments are directed to retrofit systems for existing prosthetic sockets as well as rapid response through the use of a high pressure pump and low volume actuator, and a low profile bellows design. In embodiments, a triggering algorithm utilizes measured force exceeding a threshold or thresholds with a characteristic pulse signature and a triggering of release based on a combination of total motion and measured force below a threshold or thresholds.

Other embodiments include multi-stage response, namely apply a higher pressure to the residual limb during running detection, and so on, relative to when the user is stationary. Embodiments also may track volume displacement of the residual limb as corollary to limb volume/health, and so on, and may control of pump pressure, timing, and control voltage mapped against volume. Still further embodiments detect undesirable "pistoning" of the residual limb, which is a condition where the residual limb undesirably moves in and out of the prosthetic socket along a longitudinal axis of the limb. Embodiments detect pistoning of the residual limb with an appropriate sensor and tighten the prosthetic socket around the residual limb when the sensor indicates pistoning is occurring. In addition, embodiments utilize micro-fluidic strip actuators that apply pressure to pressure distribution pads coupled to a residual limb, rather than employing fluid bladders as in some conventional approaches.

Embodiments of the present invention are described and illustrated In FIGS. 1A-9 of this application. FIG. 1A is a prosthetic device 100 according to one embodiment of the present invention. An amputee or user (these terms will be used interchangeably herein) utilizes the prosthetic device 100 to replace a missing body part, which in the example of FIG. 1A corresponds to the lower portion of a leg of the user. One skilled in the art will realize that although the embodiment of FIG. 1A and the other embodiments described in the following description are for a missing portion of a leg of a user, in other embodiments the prosthetic device 100 replaces other parts of the user's body, such as a foot, a hand, or an arm.

As seen in FIG. 1A, a user places his or her residual limb RL inside a liner 102 to cover the end portion of the residual limb that is then inserted into a socket portion or socket 104. The terms "socket portion" and "socket" may be used interchangeably below to refer to this portion prosthetic device 100, namely the portion into which the residual limb RL covered by the liner 102 is inserted. The liner 102 is made from suitable material to provide some protection for the end portion of the residual limb RL and thereby make the socket 104 more comfortable for the user to wear on the residual limb. Contained within the socket 104 are a number of hydraulic actuators 106, two of which are shown in FIG. 1A. The hydraulic actuators 106 are thus positioned between the socket 104 and liner 102 and are operable to expand and contract to thereby control the pressure that is applied to the residual limb RL through the liner 102 to thereby hold the residual limb in place within the socket. A controller 108 is coupled to the hydraulic actuators 106 and controls the expansion and contraction of these actuators. This coupling between the controller 108 and hydraulic actuators 106 is not expressly illustrated in FIG. 1A in order to simplify the figure. The controller 108 is physically located at the bottom of the socket 104 in the embodiment of FIG. 1A but may be positioned in different locations in other embodiments, and need not even be attached to the socket so long as the controller is properly coupled to control the hydraulic actuators 106. The prosthetic device 100 further includes a limb portion 110 that includes a post 112 and artificial foot 114 in the embodiment of FIG. 1A. The limb portion 110 may of course vary in different embodiments. The socket 104 in the embodiment of FIG. 1A is made from a sufficiently rigid material.

The prosthetic device 100 may be retrofitted to existing prosthetic devices including socket and limb portions as shown in FIG. 1A. The socket portion 104 is custom-designed for each user so that the socket portion properly fits onto the residual limb RL with the liner 102 placed over the limb. A prosthetist custom designs the socket portion 104 for each user and where the prosthetic device 100 is retrofitted into an existing socket the prosthetist would arrange and attach the hydraulic actuators 106 on the interior of the socket and interconnect these actuators to the controller 108. The prosthetist would also attach the controller 108 to the socket 104 and attach the post 112 to the controller as shown in FIG. 1A. This could be done in the form of a kit including the hydraulic actuators 106 and controller 108 along with any other required components for allowing the prosthetist to more easily retrofit an existing socket. In other embodiments, the hydraulic actuators 106 and controller 108 are formed as part of the socket 104 when the custom-designed socket is being made. In this situation the hydraulic actuators 106 and controller 108 may be an integral part of the socket 104. For example, electronic components of the controller 108 could be integrally formed in the socket 104 as could the required hydraulic lines interconnecting the hydraulic actuators 106 and the controller, and the same is true of the hydraulic actuators themselves.

The hydraulic actuators 106 have different structures in different embodiments, and in some embodiments the actuators utilized are not hydraulic actuators but different types of actuators that the controller 108 operates to secure the residual limb RL in the socket 106, as will be described in more detail below with reference to the remaining figures. Also note that the controller 108 senses a variety of different parameters in controlling the hydraulic actuators 106 or some other type of actuator, as will be described in more detail below specifically with reference to FIG. 8.

Figure 1B:
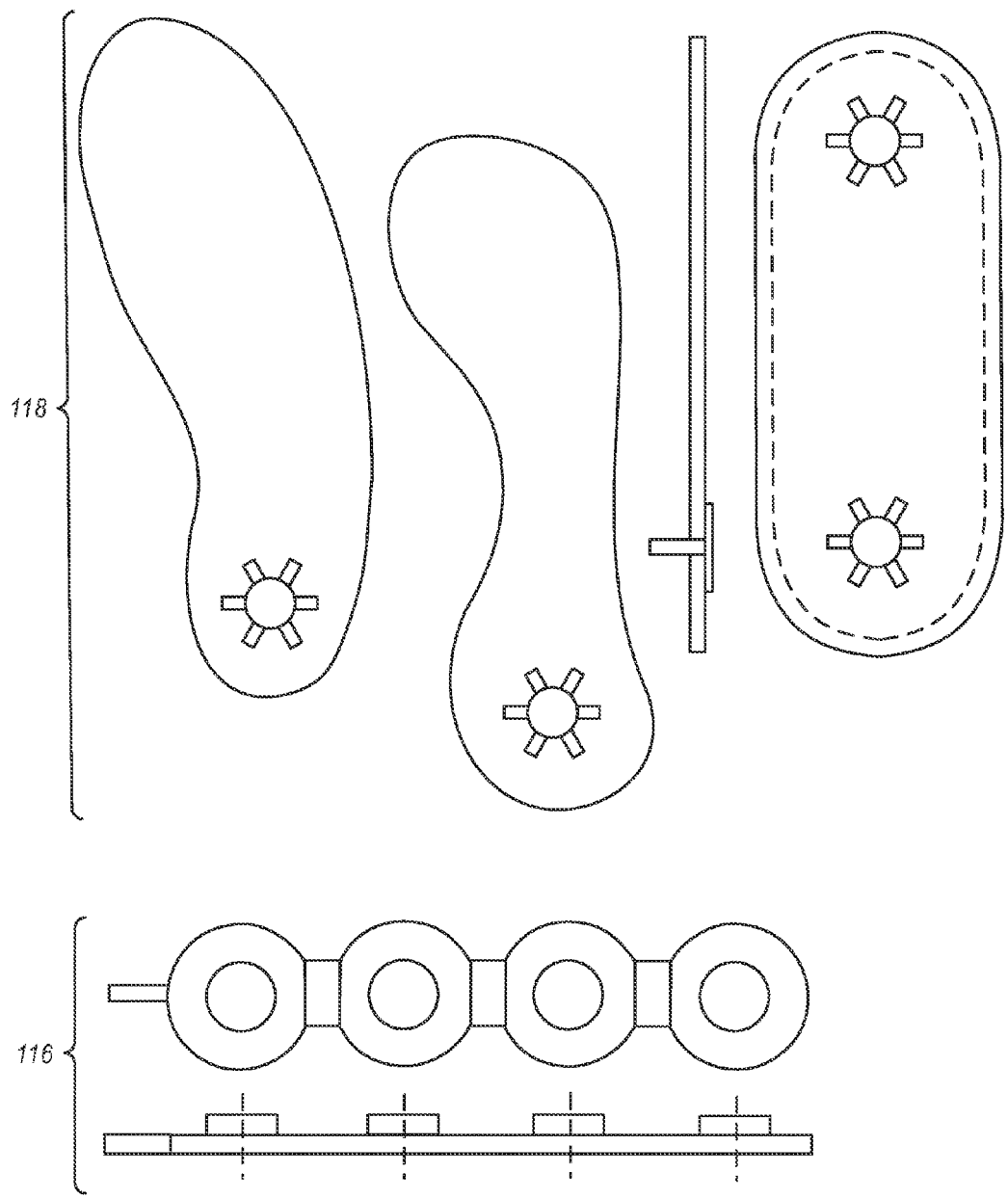
FIG. 1B illustrates two possible embodiments of the hydraulic actuators of FIG. 1A.

FIG. 1B illustrates two possible embodiments of the hydraulic actuators 106 of FIG. 1A. In the lower portion of FIG. 1B a micro-bellows 116 is one embodiment of the hydraulic actuators 106 while in the top portion of the figure a fluid pressure pad actuator 118. The fluid pressure pad actuator 118 is a semi-flexible/conformable fluid pressure pad that inserts directly between the liner 102 and the socket 104 and would typically require less reworking of the socket than does the micro-bellows actuator 116. Only small holes are required to be drilled at the base of the socket to attach the fluid pressure pad actuator 118. No changes or perhaps only very minor changes may be required to a user's existing liner 102 with this approach. The fluid pressure pad actuator 118 may be made of a heat weldable thermal plastic for attaching to the socket 104. In one embodiment, a fitting design (not shown) prevents hydraulic collapse at a plumbing interface of the actuators 118. These fluid pressure pad actuators 118 can easily be made in varying shapes. With this design, the pressure pad and actuator are essentially one integral part, as opposed to separate micro-hydraulic actuators and pressure pads. The micro-bellows actuator 116 will be described in more detail below with reference to FIG. 6A.

Figure 2:
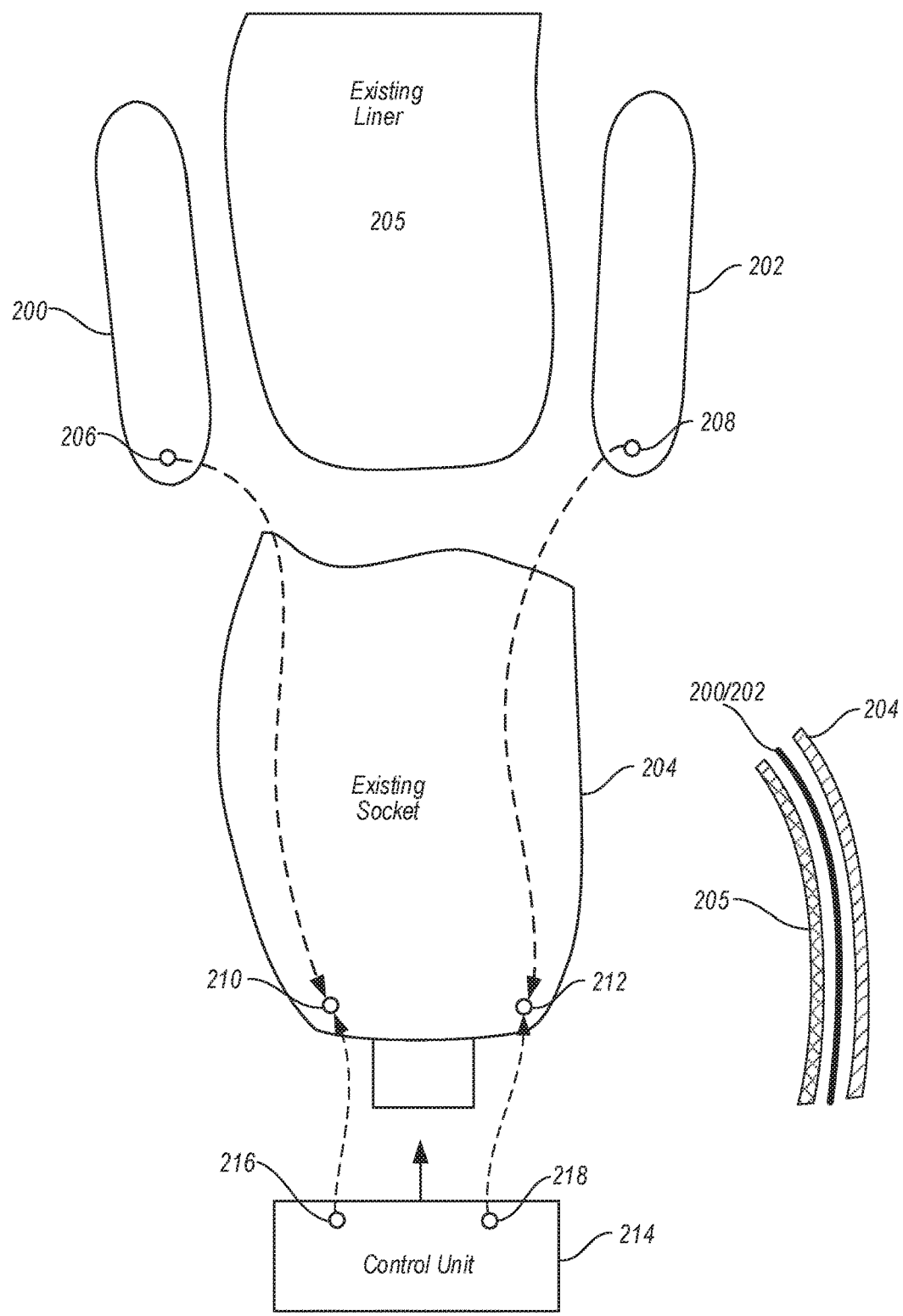
FIG. 2 is an exploded view illustrating an embodiment of the fluid pressure pads of FIG. 1B where the fluid pressure pads are utilized in retrofitting existing sockets and liners.

FIG. 2 illustrates how the fluid pressure pad actuators 118 of FIG. 1B are well-suited to retrofit applications for existing sockets and liners. In this example embodiment, fluid pressure pads 200 and 202 are mounted inside an existing socket 204 that is constructed to receive an existing liner 205. The insertion of the fluid pressure pads 200 and 202 is illustrated by the dotted lines in FIG. 2. Hydraulic fittings 206 and 208 at the bottom of each of the fluid pressure pads 200 and 202 have respective lengths sufficient to extend through holes 210 and 212 that are formed at the bottom of the socket 204. A control unit or controller 214 similarly includes hydraulic ports 216 and 218 that couple with the hydraulic fittings 206 and 208 of the fluid pressure pads 200 and 202. The right-hand portion of FIG. 2 is a cross-sectional view illustrating the position of the fluid pressure pads 200/202 between the existing liner 205 and existing socket 204.

Figure 3:
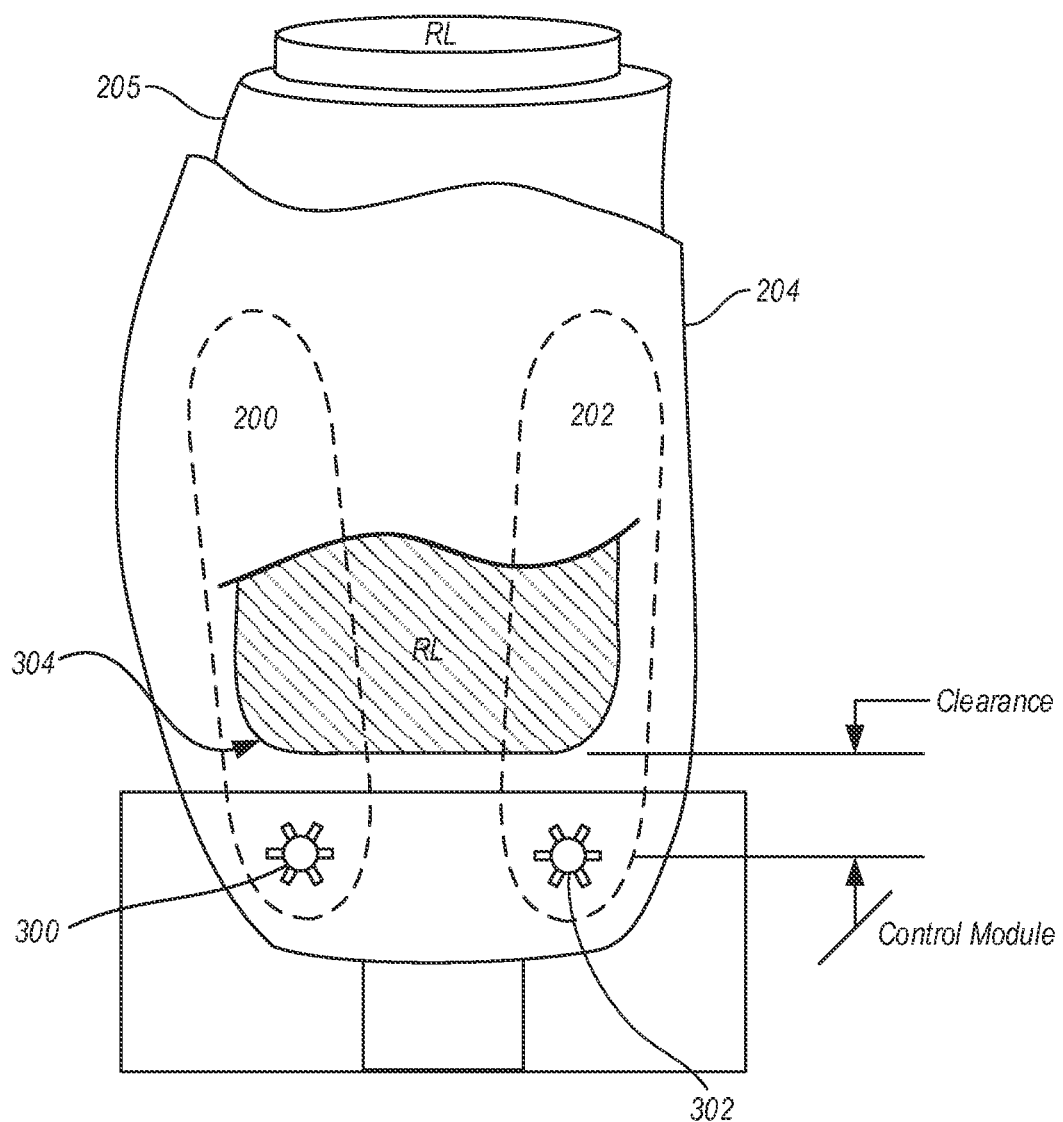
FIG. 3 illustrates the components in the exploded view of FIG. 2 when the components have been integrated or assembled to form the prosthetic device.

FIG. 3 illustrates the components in the exploded view of FIG. 2 integrated or assembled to form the corresponding prosthetic device. In this embodiment, hydraulic fitting interfaces 300 and 302, which is where the hydraulic fittings 206 and 208 couple to the hydraulic ports 216 and 218, are below the distal end 304 of the residual limb RL, thus avoiding the hydraulic collapse and pinch problems that may be associated with fluid feeder tubes being between the residual limb and the socket 204.

Figure 4:
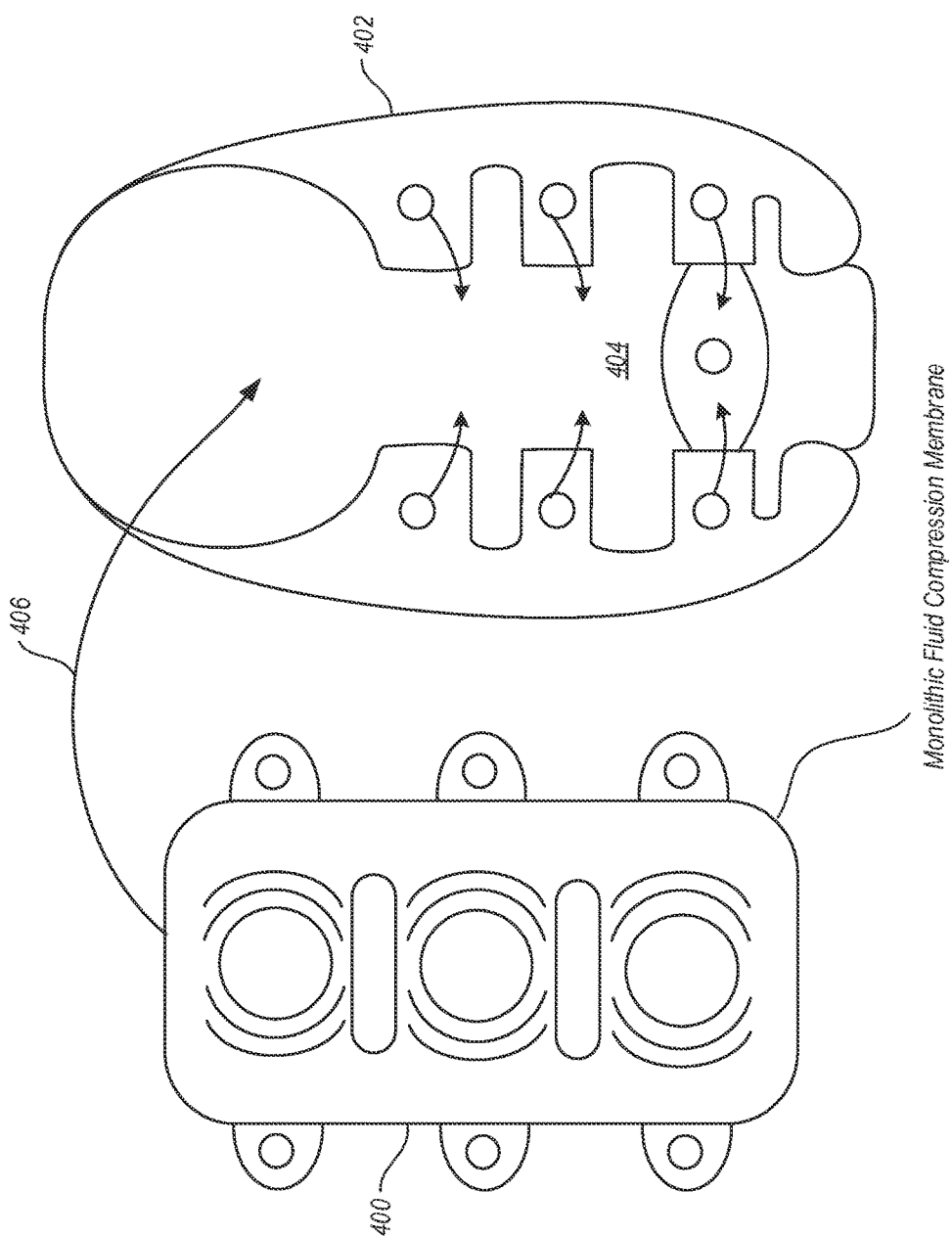
FIG. 4 illustrates another embodiment of the hydraulic actuators and socket of FIG. 1A.

FIG. 4 illustrates another embodiment of the hydraulic actuators 106 and the socket 104 of FIG. 1A. In this embodiment, hydraulic actuators 400 have a different structure as does a flexible socket 402, which in this embodiment is flexible and operates responsive to the hydraulic actuators to constrict in a circumferential direction as indicated by the arrows 404 when the hydraulic actuators are mounted in position on the flexible socket as indicated by arrow 406. With this approach the flexible socket 402 deforms due to the pressures applied by the hydraulic actuators 400 in the circumferential direction 404. The hydraulic actuators 400 would affix to the posterior side of the socket 402 (i.e. the posterior side of the socket is at the back of the user's residual limb RL). The flexible socket 402 would provide more dynamic range, particularly in the release mode. This open spine concept for the socket 402, namely where the posterior side of the socket is open as shown, may also allow improved breathability for the residual limb RL (not shown in FIG. 4) inserted in the socket. This embodiment may also provide more uniform and consistent pressure profiles applied by the socket 402 to the residual limb RL and may provide simplicity (less hardware) over multi-bladder embodiments. Active reduction of the size of the socket 402 may better address residual limb suspension, particularly when the volume of the limb is reduced.

Figure 5:
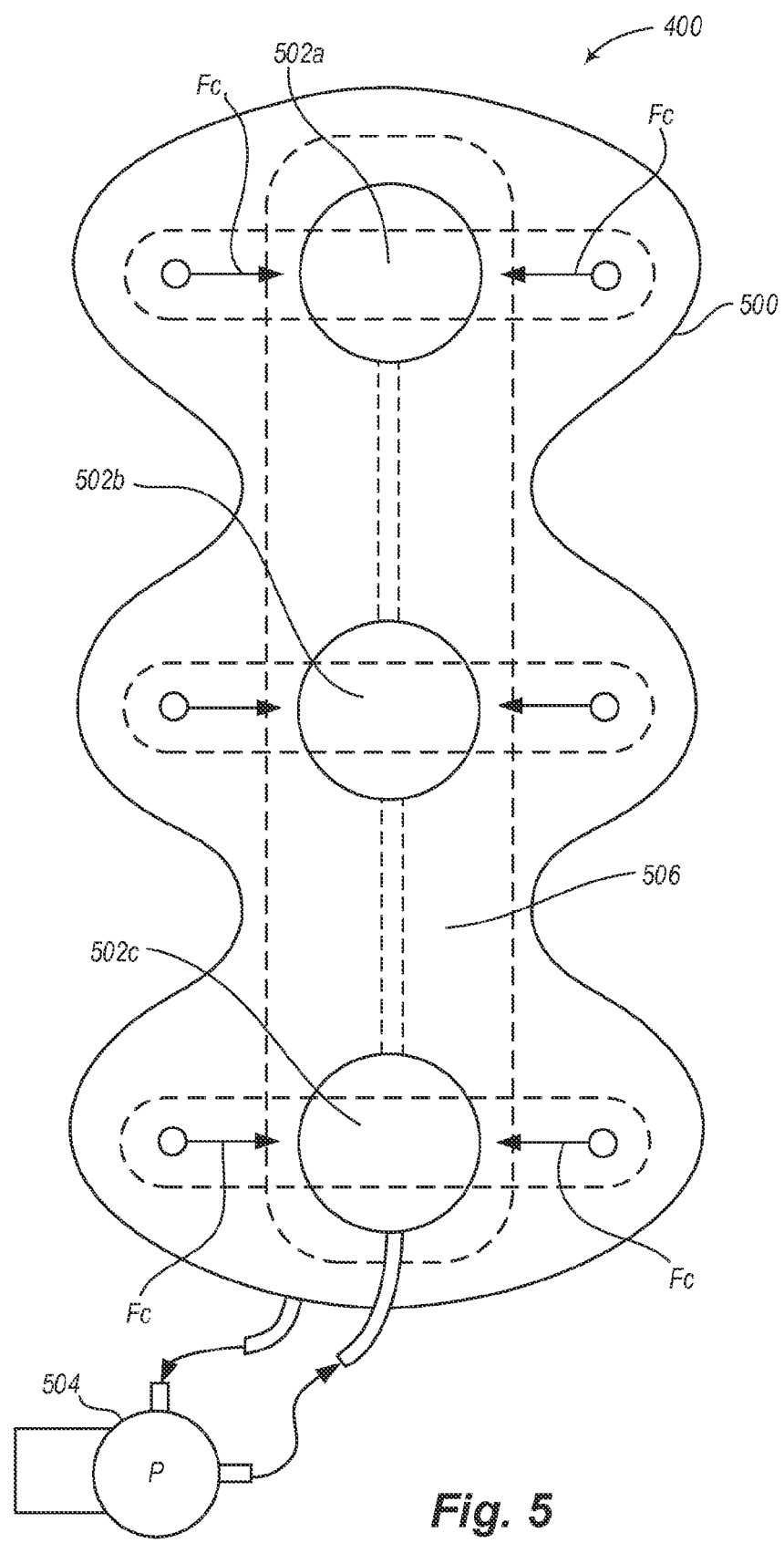
FIG. 5 is a more detailed view of the hydraulic actuator of FIG. 4.
Figure 6A:
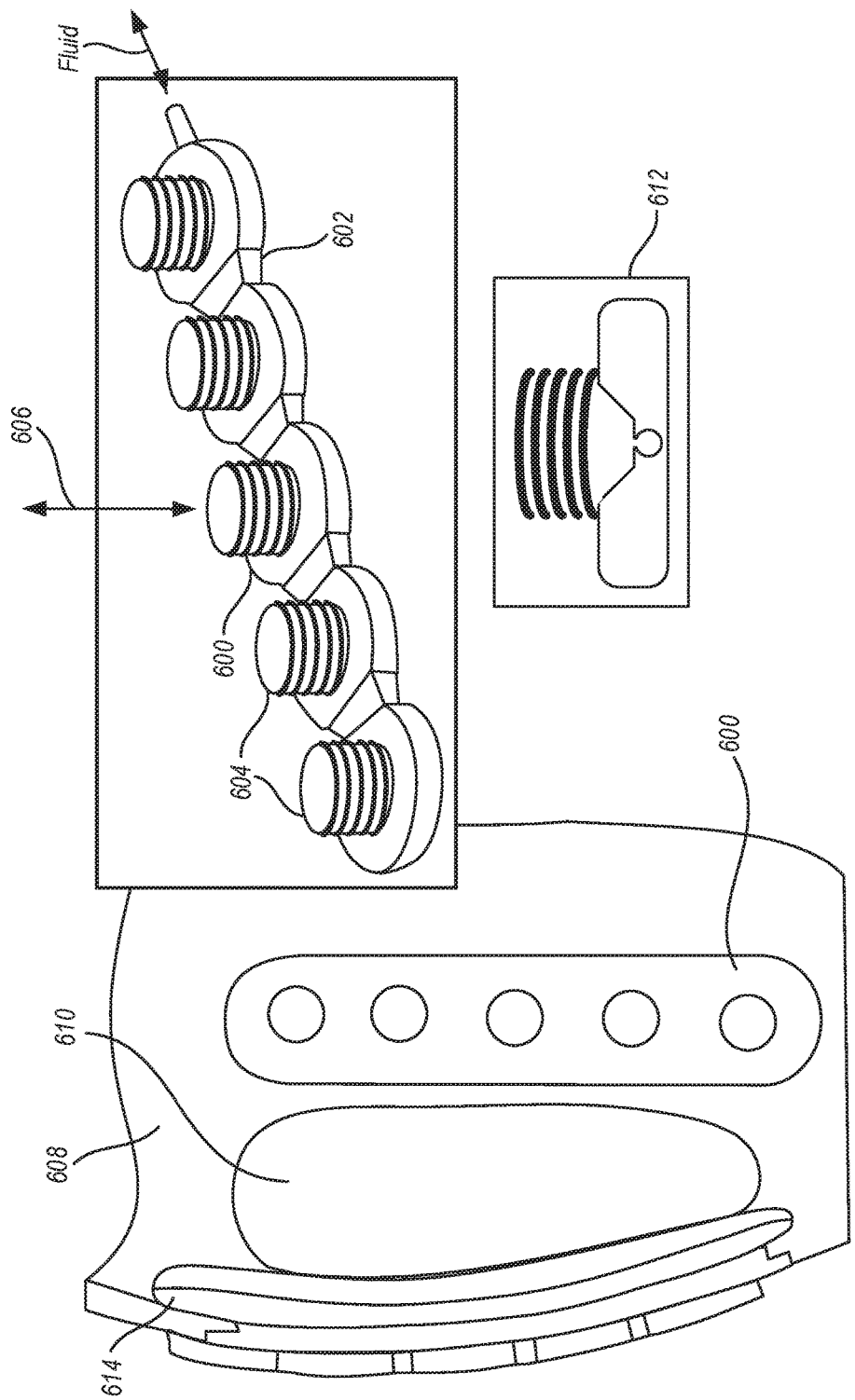
FIG. 6A illustrates several views of a micro-fluidic strip actuator corresponding to another embodiment of the hydraulic actuators of FIG. 1A.

FIG. 5 is a more detailed view of the hydraulic actuator 400 of FIG. 4. The hydraulic actuator 400 includes a constricting membrane 500 that attaches to the flexible socket 402 (FIG. 4). Contained in the membrane 500 are individual actuators 502a-c, which are coupled to a hydraulic pump 504 that controls the activation (expansion) and deactivation (contraction) of the individual actuators. Internal reservoirs 506 are formed in the membrane 500 and are used by the pump to pump a hydraulic fluid into the individual actuators 502a-c to activate the actuators or to pump fluid from the actuators into the internal reservoirs to deactivate the actuators. When the pump 504 activates the actuators 502a-c, the actuators expand, causing the membrane 500 to constrict and apply circumferential force Fc to the socket 402 (FIG. 4) and thereby increase the pressure the socket applies to the residual limb RL contained therein. Conversely, when the pump deactivates the actuators 502a-c, the actuators contract and thereby reduce the circumferential force Fc. The hydraulic actuator 400 may be a fully closed system, where the individual actuators 502a-c, internal reservoirs 506, and the pump 504 are consolidated into the membrane 500, which may be made of a monolithic elastomeric flexible material. The constricting membrane 500 can be thought of as a hydraulic muscle. FIG. 6A illustrates a micro-fluidic strip actuator 600 corresponding to another embodiment of the hydraulic actuators 106 of FIG. 1A. As seen in the embodiment of FIG. 6A, each micro-fluidic strip actuator 600 includes a plenum 602 and a number of bellows actuator portions 604 that expand or contract, as indicated by arrow 606, responsive to fluid in the plenum 602 under control of the controller 108 (FIG. 1A). A cutout or cutaway view 612 of the actuator 600 is shown in the inset view in the lower right portion of FIG. 6A. On the left hand side of FIG. 6A another cutaway view illustrates an embodiment of the actuators 600 attached to or formed as an integral part of a liner 608. A reservoir 610 holds the fluid that is pumped into and out of the actuators 600 to control the displacement of the bellows actuator portions 604 and thereby the pressure collectively applied by the actuators. The liner 608 includes for each actuator 600 a pressure distribution pad 614 positioned within the liner 608, with a respective pressure distribution pad adjoining each actuator. In operation, the controller 108 (FIG. 1A) pumps fluid into or out of the plenum 602 of each actuator 600 to control the actuation or displacement of the bellows actuator portions 604 and thereby the pressure applied to the residual limb RL (not shown in FIG. 6A) of the user. This control is discussed in more detail below with reference to FIG. 8.

Figure 6B:
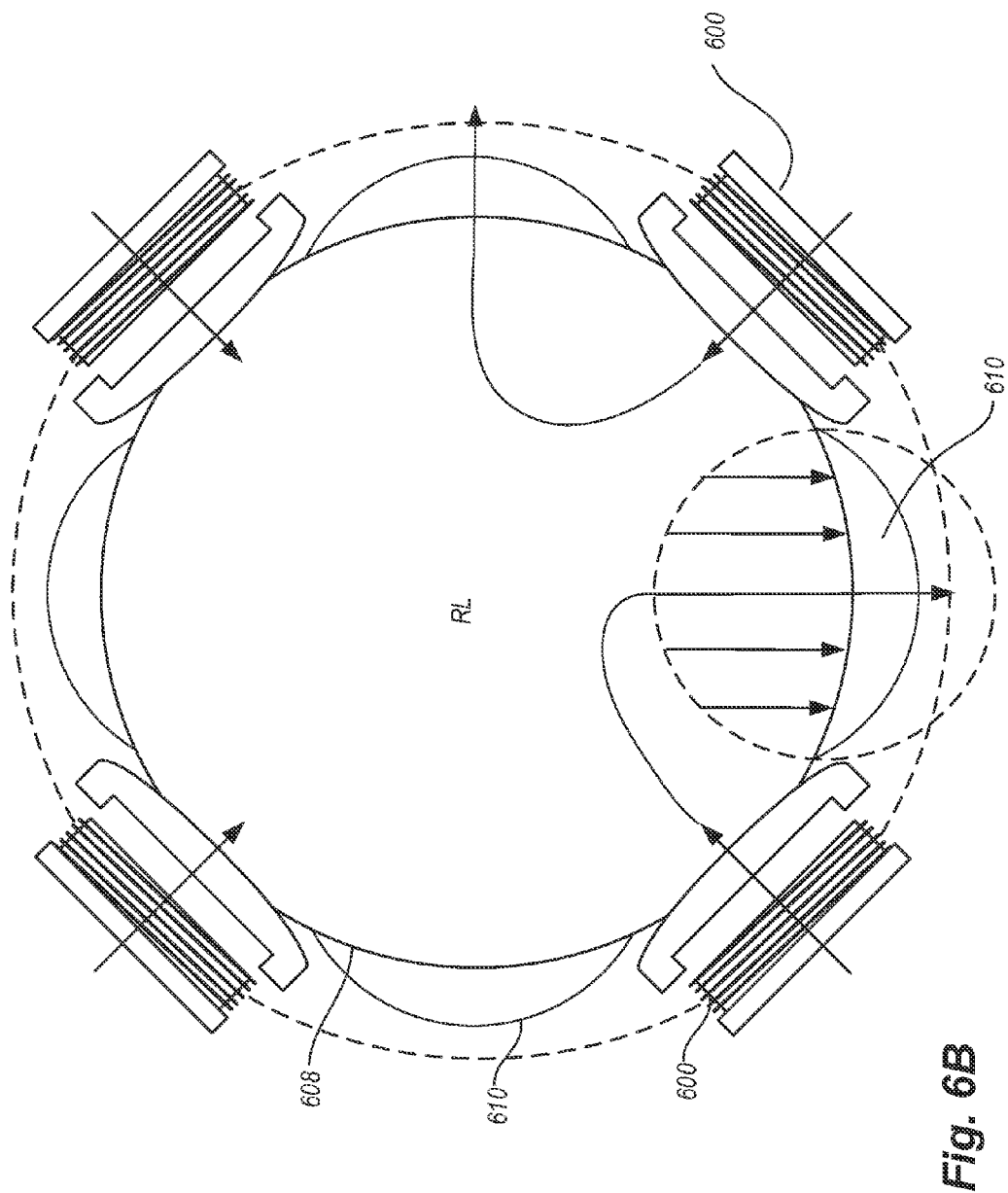
FIG. 6B is a cross-sectional view of the embodiment of FIG. 6A illustrating the position of the reservoirs between adjacent micro-fluidic strip actuators.
Figure 6C:
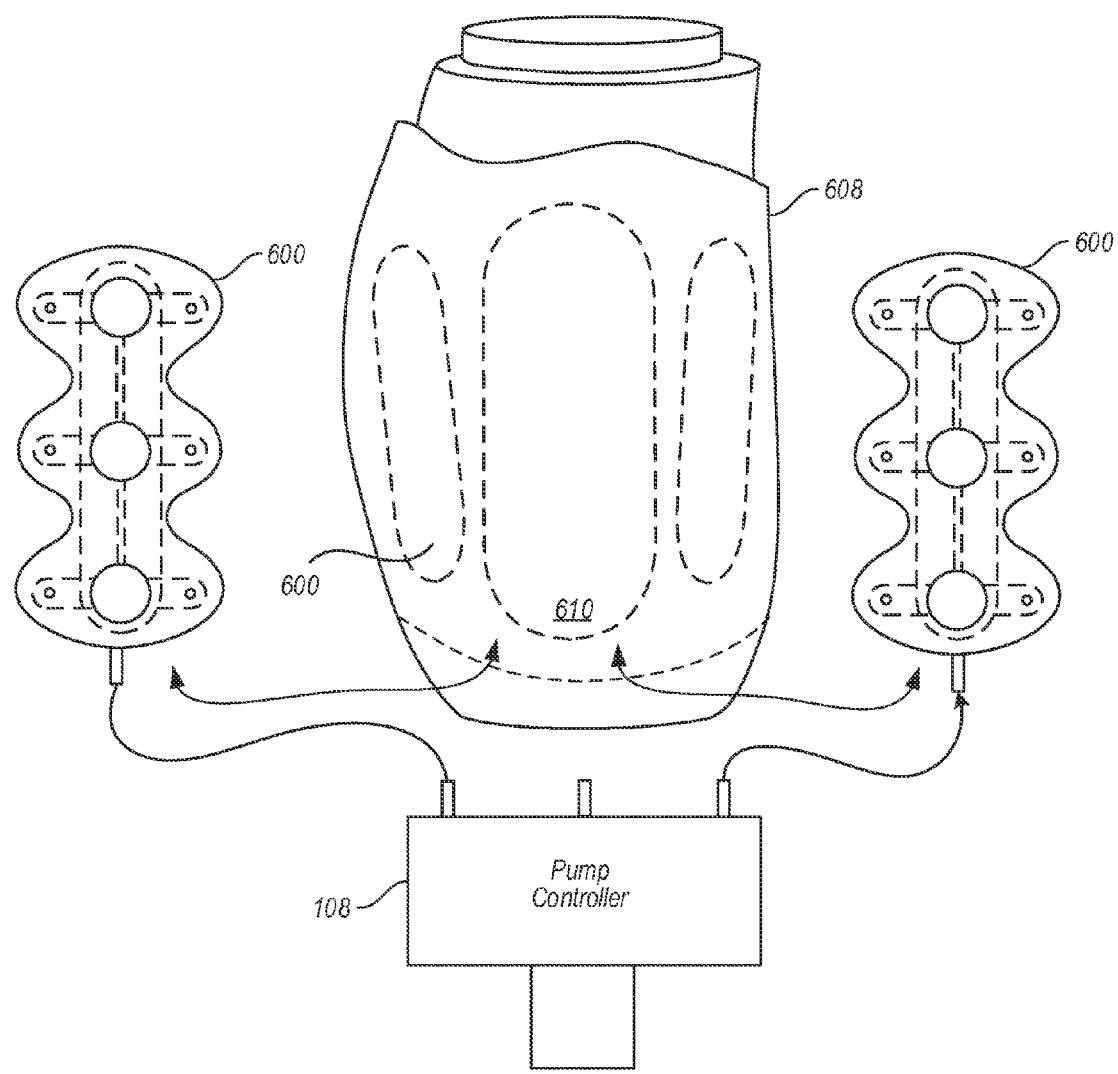
FIG. 6C illustrates the micro-fluidic strip actuator of FIG. 6A positioned within the socket of FIG. 6A and the interconnection of the controller of FIG. 1A to the micro-fluidic actuators.

FIG. 6B is a cross-sectional view of a prosthetic device including the actuators 600 and reservoirs 610 of FIG. 6A where a respective reservoir is positioned between adjacent actuators. Such a circumferentially-spaced positioning of the reservoirs 610 and the actuators 600 allows for soft tissue displacement of the residual limb RL as the actuators operate to control the pressure applied to the residual limb, as will be described in more detail below. FIG. 6C is a side view of the embodiments of FIGS. 6A and 6B and illustrates the actuators 600 positioned on the liner 608 and the interconnection of the controller 108 (FIG. 1A) to the actuators.

Figure 6D:
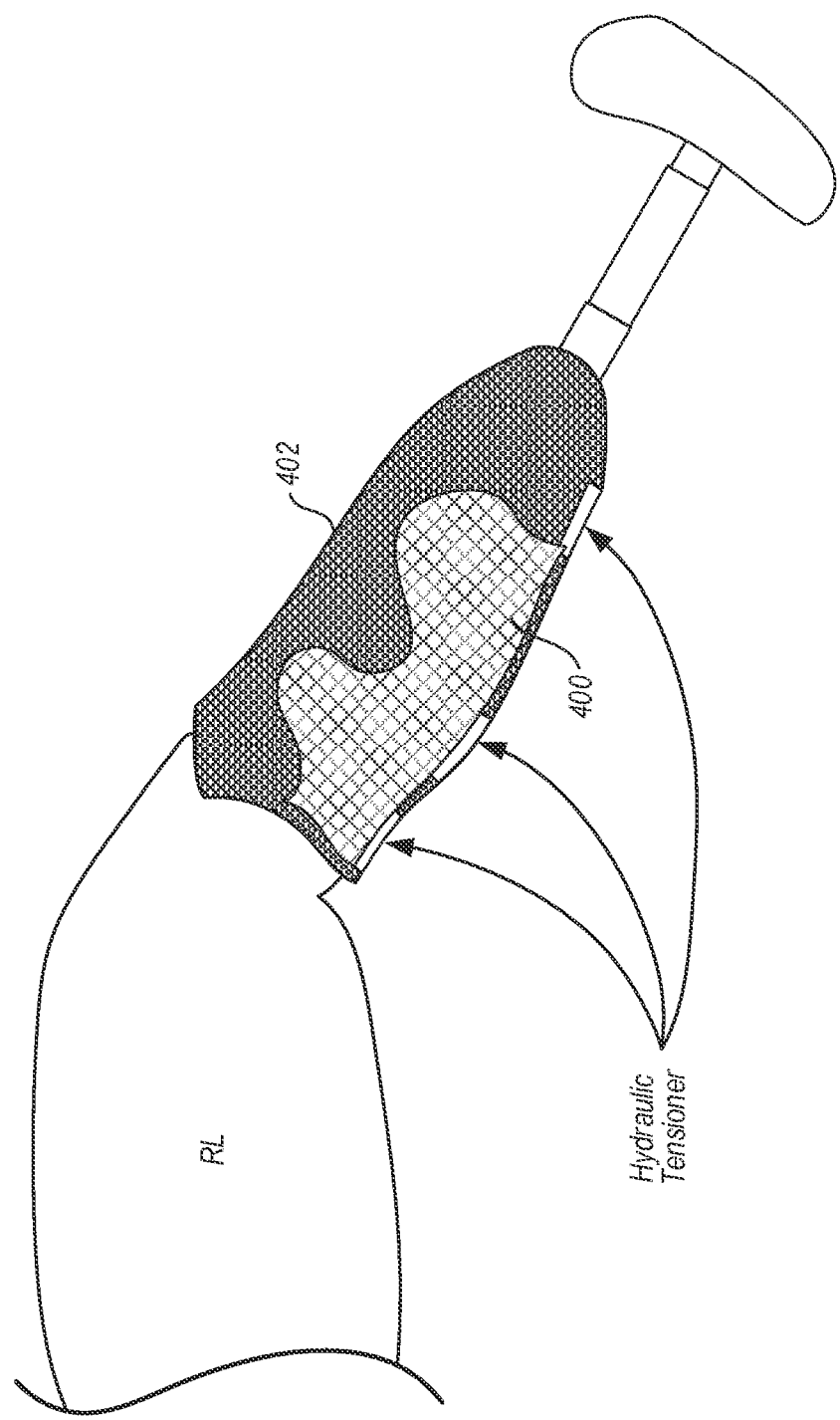
FIG. 6D illustrates the constricting actuator of FIG. 4 positioned on the residual limb of an amputee.

FIGS. 6D and 6E illustrate in more detail the actuator 400 previously discussed with reference to FIG. 4. FIG. 6D shows the actuator 400 attached to the flexible socket 402 and the prosthetic device formed by these two attached to a residual limb RL. FIG. 6E shows some more details of the prosthetic device of FIG. 6D where the hydraulic actuators 400 include an integrated reservoir.

Figure 7A:
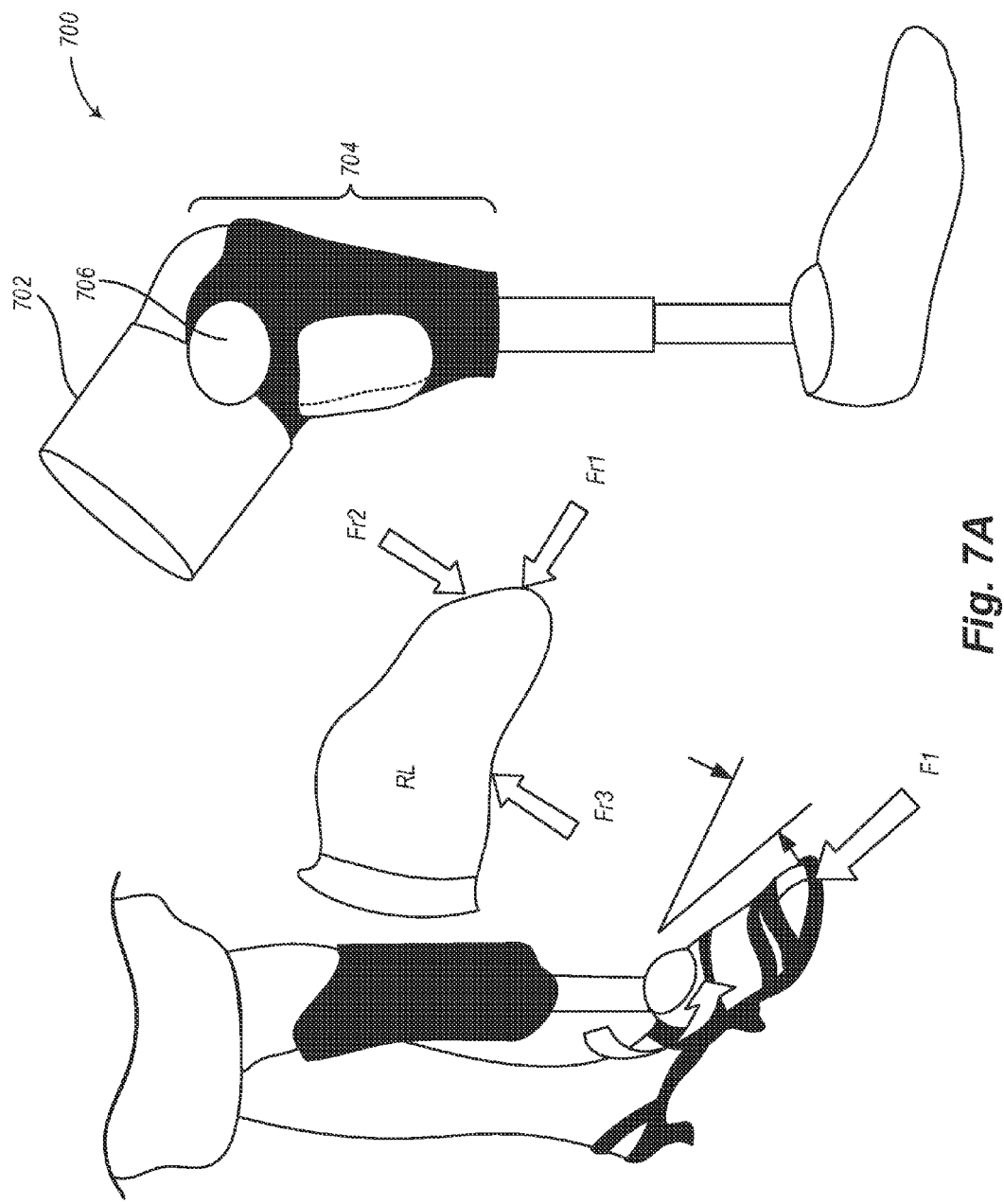
FIG. 7A illustrates a prosthetic device including a thigh compression band according to another embodiment of the present invention.
Figure 7B:
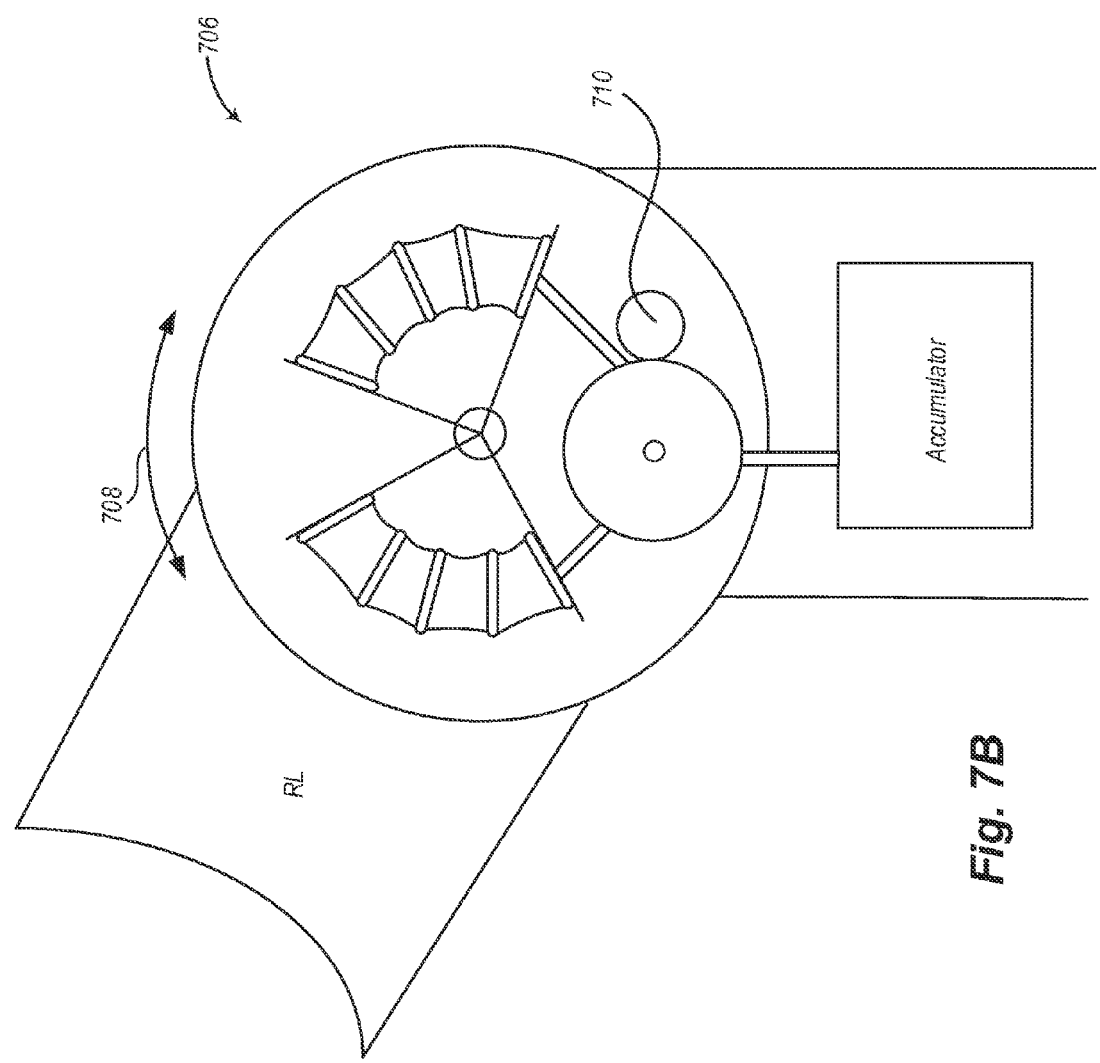
FIG. 7B illustrates one embodiment of the hinge of the prosthetic device of FIG. 7A in which the motion of the hinge is utilized to generate electrical power for powering electronic components in the prosthetic device.

FIG. 7A illustrates another embodiment of a prosthetic device 700 including a thigh compression band 702. The thigh compression band 702 operates to offset high interface pressures Fr1, Fr2, Fr3 that can result on the residual limb RL from the prosthetic device 700, particularly where the residual limb is relatively short. Thus, in this embodiment the thigh compression band 702 operates in combination with a prosthetic device portion 704 which may, for example, correspond to the prosthetic device 100 previously described with reference to FIG. 1A or the other embodiments described above. A hinge 706 interconnects the prosthetic device portion 704 and thigh compression band 702 in the illustrated embodiment. The hinge 706 may be utilized as a power source to generate electrical power for electronic components of the prosthetic device portion 704, as illustrated in FIG. 7B. The hinge 706 would do this by converting the rotational energy from the hinge, as generated by the user's movement of the hinge and indicated in the figure through the arrow 708, into electrical energy. In one embodiment, the hinge 706 includes an impeller generator 710 that converts the rotational movement 708 of the hinge 706 into electrical energy. In another embodiment, hinge 706 includes electronic circuitry to manage counter torque booth linearly and rotationally. The thigh compression band 702 may be a compression band formed from an inelastic material that is operable to apply compression to the residual limb RL.

FIG. 8 is a flowchart illustrating a control algorithm or process 800 that is executed by the controller 108 (FIG. 1A) according to one embodiment of the present invention. The specific control processor algorithm executed by the controller 108 will depend on a variety of factors, such as the particular embodiment of hydraulic actuator and prosthetic device being utilized. The process 800 may accordingly be used with the various actuator and prosthetic device embodiments described with reference to FIG. 1A-7, but may vary in the specifics of the process depending on the particular embodiments being implemented, as will be appreciated by those skilled in the art. The controller 108 includes a number of components not expressly illustrated in FIG. 1A. For example, the controller 108 includes a number of sensors that sense a variety of different parameters to control the operation of the prosthetic device 100. In addition, the controller 108 includes pumps coupled to the reservoirs (e.g., reservoirs 610 in FIG. 6A) and the actuators 106 or other actuators previously described. The controller 108 controls the pumps in response to sensed parameters to control the actuators 106 and thereby the pressure the prosthetic device 100 applies to the residual limb RL of the user.

In the embodiment of FIG. 8, the controller 108 includes three acceleration sensors that sense acceleration Ax, Ay, Az along three orthogonal axes. These acceleration sensors are suitably formed in the controller 108 or positioned on the socket 104 or elsewhere on the prosthetic device 100 in various embodiments. The controller 108 also includes suitably positioned sensors that measure the pressure P in the actuators 106 and a sensor that senses force F applied to the socket 104 by the residual limb RL of the user. In operation, the process starts in step 802 when the controller 108 is activated, which may be through a suitable switch on the controller or automatically when the user places the prosthetic device 100 on his or her residual limb RL. The process then proceeds to step 804 and reads a number of "trigger" or threshold values from a memory in the controller 108, such as an EEPROM, FLASH, or other suitable memory device. These threshold values correspond to thresholds for the sensed accelerations Ax, Ay, Az, pressure P, and force F values, with these thresholds being designated A_trig, P_trig, and F_trig, respectively. The thresholds also include a relaxation trigger threshold R_trig that is utilized by the controller 108 in determining whether to release the socket 804 from the residual limb RL, as will be described in more detail below. The pressure, force, and accelerometers may be formed from suitable MEMS devices.

From step 804 the process then goes to step 806 and the controller 108 monitors the sensed acceleration Ax, Ay, Az, pressure P, and force F values and then goes to step 808 and computes a standard deviation value A_dev for the sensed acceleration values, where the standard deviation value is the standard deviation of the total acceleration vector $(Ax^2+Ay^2+Az^2)^{1/2}$ computed over a moving window or defined time interval. The standard deviation value A_dev indicates the total motion of the prosthetic device 100. After step 808, the process goes to step 810 and determines whether the sensed force F is greater than the force threshold F_trig, indicating a maximum desirable force applied to the socket 104 by the residual limb RL of the user. If the determination in step 810 is negative, meaning the sensed force F is not greater than maximum force threshold F_trig, the process returns to step 806 and continues monitoring the sensed parameters.

When the determination in step 810 is positive, however, this means the sensed force F applied to the socket 104 by the residual limb RL is greater than the desired maximum force threshold F_trig. In this situation the process goes to step 812 and determines whether the sensed pressure P in the actuators 106 is less than the corresponding pressure threshold P_targ which indicates a target pressure to be maintained by the actuators. If the sensed pressure P is less than the target threshold P_targ, the determination in step 812 is positive and the process proceeds to step 814 and the controller 108 opens valves between the fluid reservoirs 610 (see FIGS. 6B and 6C, for example) and the actuators 106 and then proceeds to step 816 and turns the pump ON to increase the pressure P in the actuators towards the target pressure threshold P_targ.

From step 816, the process then returns to step 812 and once again determines whether the sensed pressure P in the actuators 106 is less than the target pressure threshold P_targ. The process continues executing steps 812-816 until the determination in step 812 is negative, meaning that the sensed pressure P in the actuators 106 is greater than or equal to the target pressure threshold P_targ. At this point, the process proceeds to step 818 and closes the valves to thereby maintain this pressure P in the actuators 106 and then proceeds to step 820 and turns the pump OFF, and also resets a relaxation timer to zero. The relaxation timer generates a relaxation count value R that is reset whenever the process returns to step 820. From step 820 the process then proceeds to step 822 and determines whether the sensed force F is less than the maximum force threshold F_trig. When the determination in step 822 is negative, the process returns to step 820 and the process then continues executing steps 820 and 822 so long as the sensed force F applied by the residual limb RL to the socket 104 is less than the desired maximum force threshold F_trig.

When the sensed force F applied by the residual limb RL to the socket 104 is greater than the desired maximum force threshold F_trig, the determination in step 822 is positive and the process proceeds to step 824. In step 824, the process determines whether the total acceleration as indicated by the standard deviation value A_dev is less than the acceleration trigger value A_trig. If the determination in step 824 is negative, the process returns to step 820 and the pump is kept OFF and the relaxation count value R is reset to zero.

When the determination step 824 is positive, meaning the total acceleration as indicated by the standard deviation value A_dev is less than the acceleration trigger value A_trig, the process goes to step 826 and determines whether the relaxation count value R is less than the relaxation trigger threshold R_trig. When the determination in step 826 is negative, the process returns to step 822. When the determination in step 826 is positive, however, the relaxation count value R is less than the relaxation trigger threshold R_trig indicating the socket 104 (FIG. 1A) should be fully retracted and the process goes to step 828 and fully retracts or releases the socket from the residual limb RL. From step 828 the process then goes back to step 806 and continues monitoring the sensed parameters.

The steps 822 through 828 in the process 800 function to determine whether to keep the prosthetic device 100 secured to the residual limb RL of the user or to release the prosthetic device from the residual limb. For example, while the user is walking it is obviously necessary that the prosthetic device 100 to stay secured to the residual limb RL of the user. Conversely, when the user is sitting down the prosthetic device 100 may be released or retracted from the residual limb RL. Retracting or releasing the prosthetic device 100 from the residual limb RL has advantages for the health or condition of the residual limb.

Figure 9:
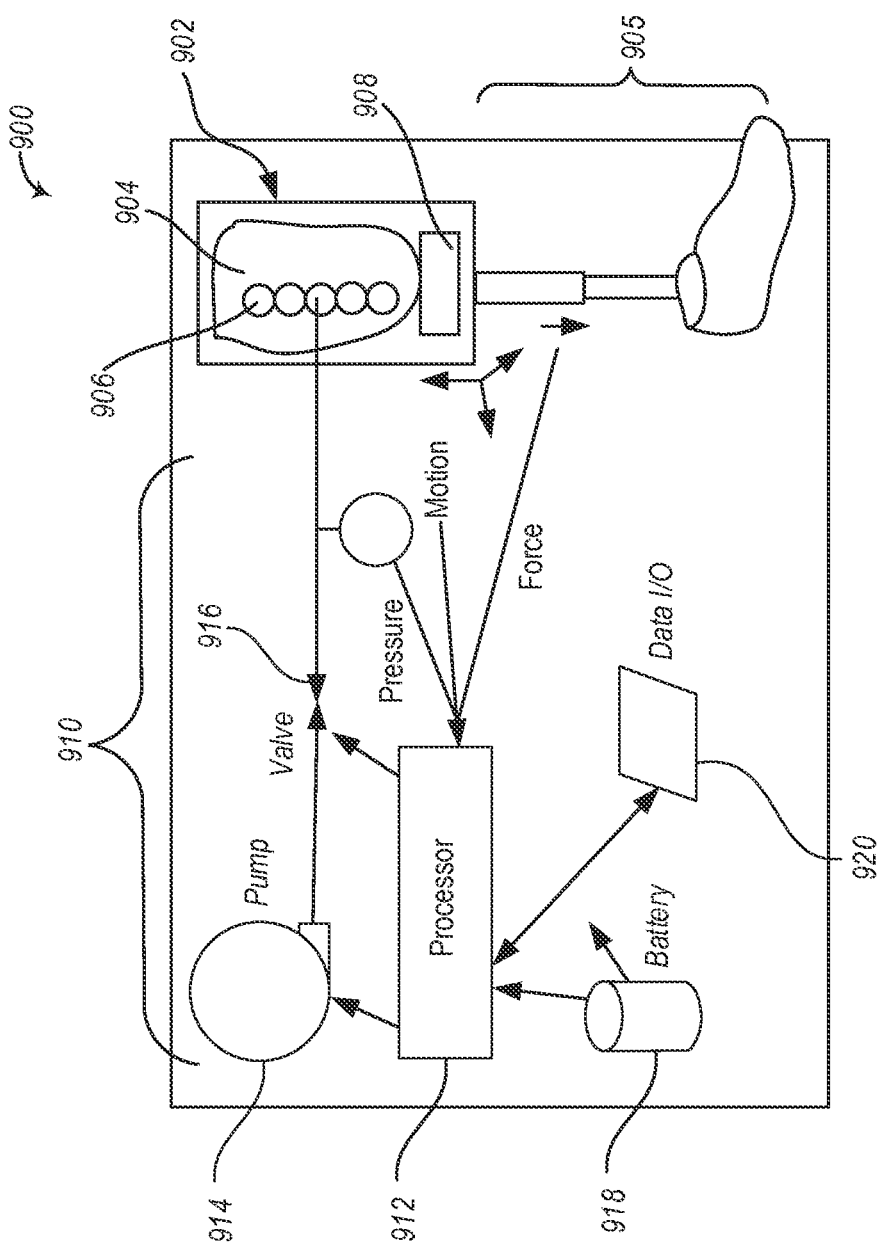
FIG. 9 is a functional block diagram of a prosthetic device according to one embodiment of the present invention.

FIG. 9 is a functional block diagram of a prosthetic device according to one embodiment of the present invention. This figure illustrates all the components of an overall system 900 that is a prosthetic device according to the above-described embodiments of the present invention. The system 900 includes the upper portion 902 of the prosthetic device and lower portion 905 of the device. The upper portion 902 includes a socket 904, actuators 906, and controller 908. The functional portion on the left of the figures illustrates components 910 contained in the controller 908, as previously described with reference to the above described embodiments. A processor 912, such as a microprocessor, microcontroller, or other suitable electronic circuitry, controls the overall operation of the system 900. The processor 912 controls a pump 914 and valves 916 coupled to the actuators 906 and reservoirs (not shown) to thereby control the pressure applied by the actuators. The processor 912 controls the pressure responsive to signals from various sensors as discussed with reference to FIG. 8. These sensors would typically include motion sensors, (accelerometers in the embodiment of FIG. 8), force sensors, and pressure sensors as indicated in FIG. 9. In operation, the processor 912 either through hardware circuitry or through processing circuitry operable to execute a series of instructions, executes the process 800 of FIG. 8, and other suitable control processes, to control the operation of the system 900. A battery 918 provides necessary power to the components 912-918. Finally, user inputs or other data inputs/outputs (I/O) 920 may also be provided to and/or from the system 900. For example, the processor 912 may communicate wirelessly with external components (not shown) such as an app running on a user's smart phone to allow the user to adjust parameters that control the operation of the system 900. The processor 912 could also wirelessly communicate data to external components such as a computer system (not shown) that the logs this data to analyze the user's use of the system 900, for example, or for other purposes. Embodiments of the present invention are directed to high speed, reversible (positive and negative pressure) distribution systems. System elements, such as the actuators, plenums, valves, and reservoirs are specifically designed to support rapid fluid transfer. In some embodiments this rapid fluid transfer allows 1-2 second execution of control processes to thereby control the fit of the prosthetic device on the residual limb RL of the user. Once placed on the residual limb RL and activated, the control is automatic and the sensors, pump, actuators, reservoirs, and so on work in unison to process human factors data with rapid response and feedback.

In some embodiments, sensors in the control loop (FIG. 8) provide go/no-go decisions in the control process, and some sensor may also provide relative degrees or continuous inputs. In some embodiments, variable pressure profiles in the control process 800 where a real time constrictive baseline is established and the socket may not always return to a zero pressure state even when the user is not moving, such as the system may remain semi-constricted in some cases even through the user is not moving, such as when the user is standing. Embodiments utilize scalable, conformal actuators that react against the socket, whether an existing socket or a modified socket. The socket, liner and the insertable/attachable actuators work in concert to provide a flexible, efficient compression system for amputees. The actuators according to embodiments of the present invention are low volume but fast response conformal actuators with adjustable contact areas, either with pressure distribution pads or insertable flat actuators that integrate pressure pad with a fluid cell.

The reservoirs according to embodiments of the present invention form a multi-purpose sub-system. The reservoirs, such as the reservoirs 610 in FIG. 6A-6C, provide positive pressure on the inlet side of the pump (i.e., where the pump is coupled to the actuator) to minimize potential for pump starvation. Moreover, the arrangement and placement of the reservoirs in the socket provides relief zones for soft tissue displacement, during compression cycles of the prosthetic device. During compression relaxation mode of operation, the reservoirs are filled and provide cushioning and even pressure distribution to support comfort and stabilization of the residual limb RL within the socket. In some embodiments, a reservoir is placed at the distal end (i.e., bottom) of the residual limb RL, possibly being integrated with the controller at the bottom of the socket. In this position, the reservoir naturally serves as a "pistoning" detection system with a pressure reference and also serves as a cushioning element. In a further embodiment, the controller may include a chiller to cool the hydraulic fluid used in the pump, actuators, and reservoirs, which may function as a comfort feature for the user of the prosthetic device.

In embodiments where a constricting socket is utilized, such as the flexible socket 402 of FIG. 4, an elastomeric hydraulic membrane may be used. This membrane can be thought of as a hydraulic muscle. Of course, this membrane is intended to serve other functions, as well, most notably to address comfort. With this approach, the socket is now more of a structural spine than a true socket. The open nature of these embodiments may provide enhanced breathability, lighter weight and increased comfort. Ultimately, the membrane may have all components (actuator, reservoir, pump, valves) integrated into a monolithic design.

In another embodiment, an inelastic compression band is utilized with hydraulic actuators to apply pressure to the liner. The band may be part of the outer or middle sheathing of the liner and functions to circumferentially constrict the liner. In another embodiment, compression cycling through the use of such an inelastic compression band could be utilized for vascular health of the user, and in such an embodiment venous insufficiency could be treated while the user is wearing the prosthetic device. In a further embodiment, the control process 800 could also function to manage a volume of the residual limb RL. In one embodiment of the system 900, the system detects the user standing given an increase in the measured force beyond a programmed threshold value. The system 900 then triggers the hydraulic pump 914 to displace the actuators 906. The control process 800 (FIG. 8) executed by the processor 912 monitors the applied pressure in the actuators, which is proportional to the applied pressure to the residual limb RL and modulates the pump in a controlled manner to reach the target pressure. Once the target pressure is achieved, the valve 916 is closed via a servo motor to hold the nominal pressure. Real time monitoring of pressure allows for automatic displacement adjustments as residual limb RL volume reduction occurs. Once the user sits an unloaded and inactive state is detected via the sensors and the pump 914 is driven in reverse to release the pressure in the interest of allowing the residual limb RL to recover volume.

Embodiments of the system 900 can be easily retrofitted to existing prosthetic sockets to provide dynamic (i.e. adaptive) zonal compression to effectively manage residual limb RL volume changes (health benefit), provide bone stabilization (improve ambulation), and substantially improve patient comfort (quality of life).

The acceleration, pressure, and force sensors integrate local body accelerations with real-time pressure reference and force sensing to make a balanced determination of when to initiate compression modes via the actuators 906. In some embodiments, the strip actuators 906 running proximal/distal (i.e., along a longitudinal axis of the residual limb RL) immediately limit bone displacement, providing essential stability between socket 904 and limb. In some embodiments, the placement of two reservoirs 610, for example, in cutout zones in the socket provide room for soft tissue displacement, supporting comfort and functional needs. The system 900 provides compression release frequently and associated with user ambulatory and non-ambulatory states, allowing effective residual limb RL fluid volume refill. Thus, embodiment of the system 900 utilize adaptive compression of the residual limb RL through an adaptive compression liner and adaptive compression socket. In some embodiments, zonal compression (e.g., anterior/posterior) is coupled with ambulatory-state detection. The residual limb RL is compressed via the actuators 906 when the user is ambulatory and the actuators release the limb when the user is non-ambulatory (i.e., stationary). In some embodiments, during a compression cycle, fluid reservoirs (see FIGS. 6A-6C) adjacent to actuators evacuate, providing a relief zone for soft tissue displacement of the residual limb RL during compression.

In the present description, certain details are set forth in conjunction with the described embodiments of the present invention to provide a sufficient understanding of the invention. One skilled in the art will appreciate, however, that the invention may be practiced without these particular details and covers other embodiments not expressly described herein. Furthermore, one skilled in the art will appreciate that the scope of the present invention is not limited to the example embodiments described, and will also understand various modifications, equivalents, and combinations of the disclosed embodiments and components of such embodiments are within the scope of the present invention. Embodiments including fewer than all the components of any of the respective described embodiments may also be within the scope of the present invention although not expressly described in detail below. Finally, the operation of well-known components and/or processes has not been shown or described in detail below to avoid unnecessarily obscuring the present invention.

What is claimed is:

1. A prosthetic device, comprising:
   a prosthetic socket including an opening configured to receive a residual limb of a user, an interior surface of the prosthetic socket being exposed through the opening and the interior surface having a circumference, the opening being on a proximal end of the prosthetic socket and the prosthetic socket including a distal end opposite the proximal end;
   a plurality of hydraulic actuators arranged circumferentially spaced apart on the interior surface of the socket;
   a plurality of hydraulic reservoirs arranged circumferentially spaced apart on the interior surface of the socket, each of the plurality of hydraulic reservoirs being positioned between adjacent ones of the plurality of hydraulic actuators, wherein each of the plurality of hydraulic actuators is a micro-fluidic strip actuator extending along a direction from the proximal end to the distal end of the prosthetic socket and extending between adjacent ones of the plurality of hydraulic reservoirs; and
   a controller physically coupled to the prosthetic socket and fluidly coupled to the plurality of hydraulic actuators and plurality of hydraulic reservoirs, the controller configured to sense a sitting state of the user and to control the plurality of hydraulic actuators to fully release the prosthetic device from the residual limb of the user in response to sensing the sitting state.

2. The prosthetic device of claim 1, wherein each of the plurality of hydraulic actuators comprises a plenum and a plurality of bellows actuator portions.

3. The prosthetic device of claim 1, further comprising a liner physically coupled to the actuators and adapted to be placed on the residual limb of the user.

4. The prosthetic device of claim 1, wherein the controller further comprises a pump and at least one pressure sensor fluidly coupled to the pump and to the plurality of hydraulic actuators, and wherein the at least one pressure sensor is configured to sense a fluid pressure in the plurality of hydraulic actuators.

5. The prosthetic device of claim 4, wherein the controller is further configured to generate a relaxation time value indicating the time after the fluid pressure in the plurality of hydraulic actuators has reached a pressure threshold value, and wherein the controller is configured to fully release the prosthetic device from the residual limb in response to the relaxation time value reaching a relaxation time threshold value.

6. The prosthetic device of claim 5, wherein the controller further comprises a relaxation timer configured to generate a relaxation count having a value indicating the relaxation time value.

7. The prosthetic device of claim 6, wherein the controller further comprises a force sensor configured to sense a force applied to the prosthetic socket by the residual limb and a motion sensor configured to sense motion of the prosthetic socket, and wherein the controller is further configured to fully release the prosthetic device from the residual limb in response to the relaxation count value reaching the relaxation time threshold value only if both the sensed force and sensed motion are less than a force threshold and motion threshold, respectively, during a time interval corresponding to the relaxation time value.

8. The prosthetic device of claim 4, wherein the controller further comprises a fluid reservoir fluidly coupled to the pump and positioned at the distal end of the prosthetic socket.

* * * * *